United States Patent
Rafter (10) Patent No.: US 7,862,511 B2
(45) Date of Patent: Jan. 4, 2011

(54) ULTRASOUND IMAGING METHOD AND APPARATUS

(75) Inventor: Patrick G. Rafter, Windham, NH (US)

(73) Assignee: Koninkliljke Philips Electronics N.V., Eindhoven (NL)

( * ) Notice: Subject to any disclaimer, the term of this patent is extended or adjusted under 35 U.S.C. 154(b) by 575 days.

(21) Appl. No.: 10/572,155

(22) PCT Filed: Oct. 14, 2004

(86) PCT No.: PCT/IB2004/052087
§ 371 (c)(1), (2), (4) Date: Mar. 16, 2006

(87) PCT Pub. No.: WO2005/039418
PCT Pub. Date: Mar. 6, 2005

(65) Prior Publication Data
US 2007/0078344 A1    Apr. 5, 2007

Related U.S. Application Data (60) Provisional application No. 60/513,630, filed on Oct. 23, 2003.

(51) Int. Cl.
A61B 8/00 (2006.01)
(52) U.S. Cl. .................. 600/458; 600/450
(58) Field of Classification Search ........... 600/458, 600/428, 437, 440, 420, 410, 459, 450
See application file for complete search history.

(56) References Cited

U.S. PATENT DOCUMENTS

| | | | |
|---|---|---|---|
| 5,195,521 A | | 3/1993 | Melton, Jr. et al. |
| 5,735,281 A | | 4/1998 | Rafter et al. |
| 5,947,904 A | * | 9/1999 | Hossack et al. ............. 600/458 |
| 5,993,390 A | * | 11/1999 | Savord et al. ............... 600/437 |
| 6,015,384 A | * | 1/2000 | Ramamurthy et al. ....... 600/440 |
| 6,030,344 A | | 2/2000 | Guracar et al. |
| 6,056,691 A | * | 5/2000 | Urbano et al. .............. 600/443 |
| 6,102,858 A | | 8/2000 | Hatfield et al. |
| 6,302,846 B1 | * | 10/2001 | Gardner ...................... 600/458 |
| 6,340,348 B1 | * | 1/2002 | Krishnan et al. ............ 600/447 |
| 6,398,732 B1 | | 6/2002 | Brock-Fisher et al. |
| 6,425,869 B1 | * | 7/2002 | Rafter et al. ................ 600/458 |
| 6,428,477 B1 | | 8/2002 | Mason |
| 6,485,423 B2 | * | 11/2002 | Angelsen et al. ............ 600/458 |
| 6,575,910 B2 | | 6/2003 | Averkiou et al. |

(Continued)

Primary Examiner—Eric F Winakur
Assistant Examiner—Lawrence N Laryea (57) ABSTRACT

A method of generating three-dimensional (3D) full volume ultra-sound images with the uses of contrast agents includes acquiring ultrasound image data for multiple subvolumes (140,142,144,146) synchronized to an ECG (100) over multiple cardiac cycles (124,126,128,130) via triggering (104, 114,106,116,108,118,110,120). Acquiring includes at least one of two acquisition protocols. The first acquisition protocol uses an output acoustic power insufficient for causing destruction of the contrast agents during ultrasound image data acquisition (10). The second acquisition protocol uses an output acoustic power sufficient for causing destruction of the contrast agents during ultrasound image data acquisition (10). Triggering (26,28) of respective ones of the ultrasound image data acquisitions of the multiple subvolumes (140,142, 144,146) is selected to enable destroyed contrast agents to be replaced by new contrast agents prior to a subsequent triggering of ultrasound image data acquisition of a subsequent subvolume. Furthermore, ultrasound image data (22) from the multiple subvolumes is combined to generate the 3D full volume 15 ultrasound image data (24).

38 Claims, 9 Drawing Sheets

U.S. PATENT DOCUMENTS

| | | |
|---|---|---|
| 6,607,490 B2 | 8/2003 | Ogasawara et al. |
| 6,730,036 B2 * | 5/2004 | Rafter et al. ................ 600/458 |
| 2001/0005776 A1 * | 6/2001 | Holley et al. ................ 600/458 |
| 2003/0092991 A1 | 5/2003 | Sehgal |
| 2003/0114750 A1 * | 6/2003 | Brock-Fisher et al. ...... 600/431 |
| 2003/0163048 A1 * | 8/2003 | Rafter et al. ................ 600/458 |
| 2004/0092816 A1 * | 5/2004 | Ossmann et al. ............ 600/428 |

* cited by examiner

ULTRASOUND IMAGING METHOD AND APPARATUS

CROSS REFERENCE TO RELATED APPLICATION

This application claims the benefit of U.S. provisional application Ser. No. 60/513,630 filed Oct. 23, 2003, which is incorporated herein by reference.

The present disclosure generally relates to medical ultrasound imaging, and, more particularly, to methods and apparatus using ultrasound contrast agents to determine more accurate volumes.

Ultrasonic diagnostic imaging systems are capable of imaging and measuring the physiology within the body in a completely noninvasive manner. Ultrasonic waves are transmitted into the body from the surface of the skin and are reflected from tissue and cells within the body. The reflected echoes are received by an ultrasonic transducer and processed to produce an image or measurement of blood flow. Diagnosis is thereby possible with no intervention into the body of the patient.

Materials known as contrast agents can be introduced into the body to enhance ultrasonic diagnosis. Contrast agents are substances which strongly interact with ultrasonic waves, returning echoes which may be clearly distinguishable from those returned by blood and tissue. One class of substances which has been found to be especially useful as an ultrasonic contrast agent is gases, in the form of tiny bubbles called microbubbles.

Microbubbles present a significant acoustic impedance mismatch in the body, and nonlinear behavior in certain acoustic fields which is readily detectable through special ultrasonic processing. Gases that have been stabilized in solutions in the form of tiny microbubbles are infused into the body and survive passage through the pulmonary system and circulate throughout the vascular system. Microbubble contrast agents are useful for imaging the body's vascular system, for instance, as the contrast agent can be injected into the bloodstream and will pass through veins and arteries of the body with the blood supply until filtered from the blood stream in the lungs, kidneys and liver.

Echocardiographic ultrasonic imaging systems are used to assess the performance of the heart. Cardiac performance can be assessed qualitatively with these systems, such as by observing the blood flow through vessels and valves and the operation of heart valves. Quantitative measures of cardiac performance can also be obtained with such systems. For instance, the velocity of blood flow and the sizes of organs and cavities such as a heart chamber can be measured. These measures can produce quantified values of cardiac performance such as ejection fraction and cardiac output.

With respect to the heart, determination of accurate and reproducible left ventricle (LV) volumes and ejection fraction have been shown to be important prognostic indicators. Such accurate and reproducible determinations have thus long been a goal of ultrasonic imaging systems. With ever increasing incidence of congestive heart failure and the necessity to closely monitor patients afflicted with the same, the importance of such measurements will undoubtedly increase.

Recent image quality improvements, in particular, harmonic imaging, have dramatically improved visualization of endocardial borders. However, despite the improvements demonstrated with harmonic imaging, there still exists a significant number of patients in which visualization of endocardial borders remains extremely challenging. In relation thereto, ultrasound contrast agents have been approved by the FDA to aid in the visualization of endocardial borders on such patients.

With the improved visualization of the borders offered by harmonic imaging and contrast agents, attempts have been made with a single plane of ultrasound data (i.e., in two dimensions) to measure the volume of the heart throughout the cardiac cycle. Of particular importance are the end-diastolic volume and the end-systolic volume, since they are representative of when the LV is typically at its maximum and minimum volume, respectively. However, an accurate measurement with one plane of ultrasound is problematic since it is necessary to make an assumption regarding the symmetry of the heart. This leads to inaccurate calculations. Using multiple planes has been shown to make the calculation much more robust; however, the planes must be acquired at different times. Also, great care has to be taken to get the correct slices of the heart through the apex (e.g., without foreshortening). This often leads to errors in the calculations also.

Furthermore, as noted above, contrast has been used in two dimensions to make estimates of volumes by assuming some symmetrical shape to the LV cavity. Also, acquiring two views at different times where one has to move the transducer to view another slice of the LV cavity has been done.

Accordingly, an improved method of acquiring ultrasound images for overcoming the problems in the art is desired.

According to an embodiment of the present disclosure, a method of generating three-dimensional (3D) full volume ultrasound images with the use of contrast agents comprising acquiring ultrasound image data for multiple subvolumes synchronized to an ECG over multiple cardiac cycles via triggering. Acquiring includes at least one of two acquisition protocols. A first acquisition protocol includes using an output acoustic power low enough for a low level of nonlinear tissue signal but sufficient enough to get a strong response from the contrast agents (e.g., the microbubbles) during ultrasound data acquisition. In order to get a sufficiently strong signal from the contrast agents (e.g., the microbubbles), power levels that cause some level of microbubble destruction when imaging at real-time update rates (e.g., 15-20 Hz) during ultrasound image data acquisition are often necessary. A second acquisition protocol includes using an output acoustic power sufficient for causing destruction of the contrast agents during ultrasound data acquisition.

Triggering of respective ones of the ultrasound image data acquisitions of the multiple subvolumes is selected in a manner to enable destroyed contrast agents to be replaced by new contrast agents prior to a subsequent triggering of ultrasound image data acquisition of a subsequent subvolume. In addition, ultrasound image data from the multiple subvolumes is combined to generate the 3D full volume ultrasound image data.

According to embodiments of the present disclosure, a method and apparatus utilize a matrix probe and live three-dimension (3D) to obtain more accurate left ventricle (LV) volumes using contrast agents and by acquiring subvolumes triggered at end systole and end diastole, as discussed further herein.

With respect to cardiac ultrasound imaging, anatomy such as the left ventricle is inherently three-dimensional. To obtain an accurate volume measurement of the left ventricle, three-dimensional data must be acquired. A goal in three-dimensional cardiac imaging is to obtain an accurate measure of the volume of the left ventricle in both end systole and end diastole, so that ejection fraction and cardiac output can be estimated. Accordingly, a need exists for improved methods and apparatus for three-dimensional cardiac ultrasound imaging.

According to one embodiment of the present disclosure, a method includes acquiring ultrasound image data representative of three-dimensional volume segments of an image volume of interest in a patient in synchronism with portions of cardiac cycles of the patient, and combining the image data representative of the volume segments to provide image data representative of a three-dimensional ultrasound image of the volume. In one embodiment, the image data acquisition is synchronized to (i.e., triggered at) the end diastole and end systole phases of the patient's cardiac cycle, so that the corresponding image represents the image volume at the respective phase. In other words, image data for a given three-dimensional subvolume segment is acquired in synchronism with a respective end diastole and end systole phase in each of a number N of successive cardiac cycles of the patient. The corresponding ones of the three-dimensional images may be displayed following completion of image data acquisition for the image volume.

Contrast agents have been found to provide a second harmonic response to impinging ultrasound energy at a corresponding fundamental excitation frequency. This second harmonic response energy can be used to provide increased diagnostic information about surrounding tissues within a given proximity to the contrast agents. A second harmonic response occurs when an agent under increasing ultrasonic pressure, "maps" energy into the harmonics of the fundamental frequency, in addition to the fundamental. However, when microbubble based contrast agents resonate when driven with a high enough power, they can be destroyed. If the acoustic power is high enough, the microbubble can be destroyed after one pulse. However, microbubble destruction can still occur at low acoustic powers if a microbubble is imaged with multiple pulses.

Moreover, contrast agents resonate in the presence of an ultrasound field and a resultant echo signal can be received and detected by any suitable ultrasound scanner. Higher transmit powers increase a backscattering cross section of the microbubbles, particularly in harmonic mode. Accordingly, the microbubbles scatter a larger portion of the impinging ultrasound signal. However, the duration of the contrast effect is shorter at high power levels, due to increased microbubble destruction and resultant lower concentration(s) of microbubbles. Accordingly, the imaging sequences as disclosed herein can be used to assist in optimizing an overall contrast effect provided via use of microbubbles.

Furthermore, in connection with the above discussion, contrast agents can be destroyed at low MI's (0.1) at normal frame rates (i.e., 15-20 Hz). A single frame of ultrasound at that same MI will not necessarily destroy the microbubble, that is, it may take many more frames to destroy it. Accordingly, in one embodiment, dual trigger does not require an acoustic output power such that it can destroy the microbubble by hitting it just once in order to be effective. The fact that microbubbles have less ultrasound exposure makes the enhancement last longer. The embodiments of the present disclosure seek to minimize destruction by minimizing the ultrasound exposure while maximizing signal to noise at the same time. Hitting a bubble thirty (30) times at an MI of 0.1 could destroy it, but hitting the same bubble two (2) times at an MI of 0.2 (twice as hard) might not destroy it. The MI of 0.2 has higher signal to noise for at least two reasons—more bubbles to image and stronger signals coming back from the bubbles due to the stronger transmit signal. The embodiments also include the case where the output acoustic energy provides a high enough MI (e.g., on the order of 0.7 or higher depending on the particular contrast agent for a particular application) to destroy the microbubble by hitting it once as well. In this case, the extra time between triggerings allows for replenishment of destroyed microbubbles with new microbubbles.

In accordance with one embodiment of the present disclosure, an imaging sequence is synchronized with a patient's ECG, allowing for a desired series of frames to be obtained, further as discussed herein. The imaging sequence utilizes dual triggering per cardiac cycle, for a series of cardiac cycles. A series of acquired sub-volumes allow for being combining together to form a complete volume image of a portion of the heart cycle from multiple heart cycles. The imaging sequence as discussed herein is selected for controlling an amount of microbubble destruction (i.e., minimizing an overall microbubble destruction), thereby allowing for a prolonged contrast effect. As a result, endocardial border detection, which is needed for the determination of ejection fraction and volume calculations, is enhanced and accordingly makes the determination thereof easier.

Figure 1:
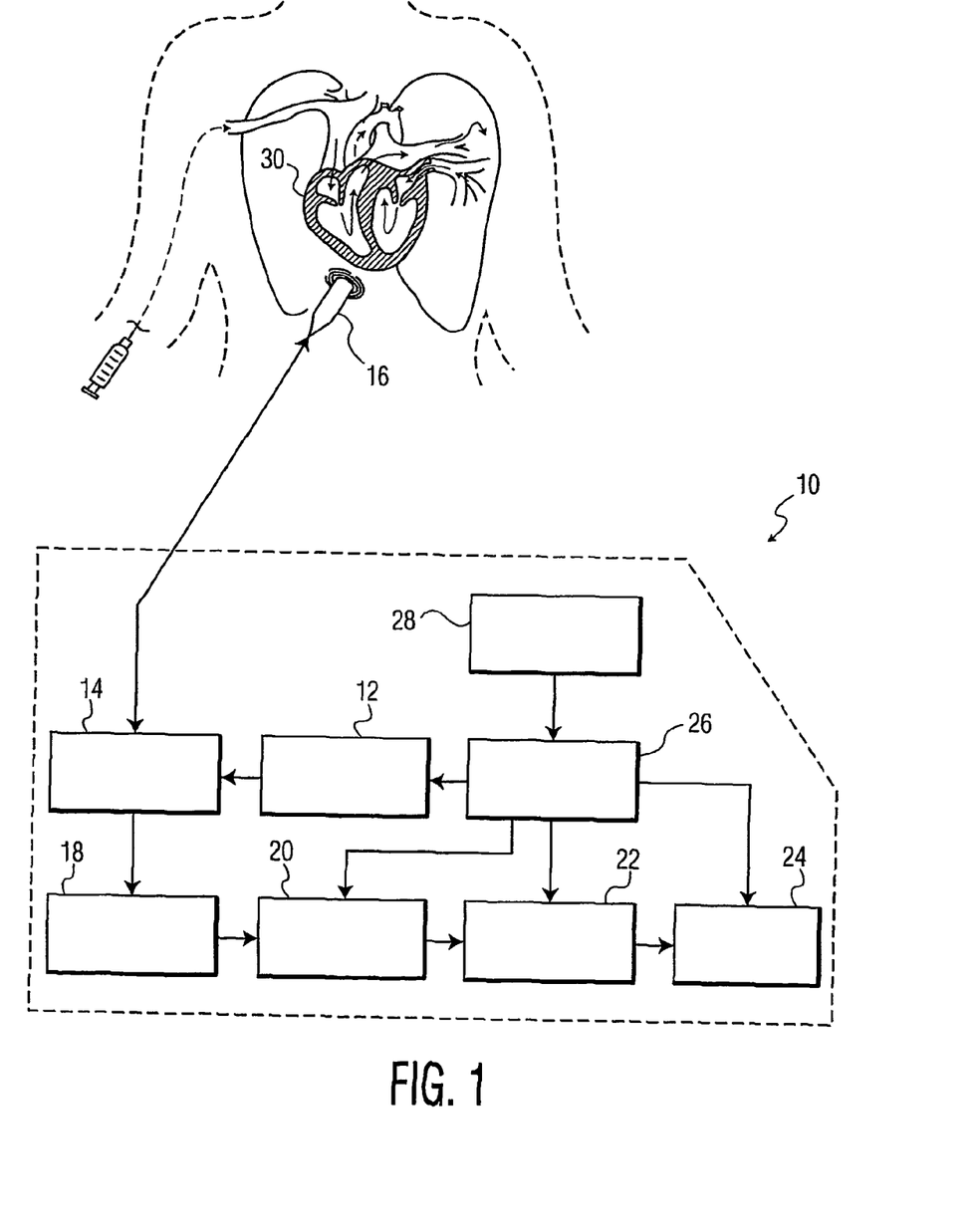
FIG. 1 is a block diagram view of an ultrasound diagnostic imaging system suitable for implementing one embodiment of the present disclosure.

FIG. 1 is a block diagram view of an ultrasound diagnostic imaging system 10 suitable for implementing the various embodiments of the present disclosure. An ultrasound transmitter 12 is coupled through a transmit/receive (T/R) switch 14 to a transducer array 16. Transducer array 16 comprises a two-dimensional array of transducer elements for performing three-dimensional scanning. The transducer array 16 transmits ultrasound energy into a region being imaged and receives reflected ultrasound energy, or echos, from various structures and organs within the patient's body. The transmitter 12 includes a transmit beamformer. By appropriately delaying the pulses applied to each transducer element by transmitter 12, the transmitter transmits a focused ultrasound beam along a desired transmit scan line.

According to one embodiment, array transducer 16 includes a two dimensional array such as disclosed in U.S. Pat. No. 6,428,477, assigned to the assignee of the present disclosure and incorporated herein by reference. U.S. Pat. No. 6,428,477 discloses delivery of therapeutic ultrasound and performing ultrasound diagnostic imaging with the use of a two dimensional ultrasound array. The two dimensional ultrasound array includes a matrix or "grid" of transducer elements. Having a grid or matrix of transducer elements allows three-dimensional (3D) images to be acquired. That is, the matrix of transducer elements makes possible the steering and electronic focusing of ultrasound energy in any arbitrary direction. Unlike the two dimensional ultrasound array, a typical single array of transducer elements allows steering and electronic focusing in only one plane.

The transducer array 16 couples to an ultrasound receiver 18 through T/R switch 14. Reflected ultrasound energy from a given point within the patient's body is received by the transducer elements at different times. The transducer elements convert the received ultrasound energy to received electrical signals which are amplified by receiver 18 and are supplied to a receive beamformer 20. The signals from each transducer element are individually delayed and then are summed by the beamformer 20 to provide a beamformer signal that is a representation of the reflected ultrasound energy level along a given receive scan line. As known in the art, the delays applied to the received signals may be varied during reception of ultrasound energy to effect dynamic focusing. The process is repeated for multiple scan lines to provide signals for generating an image of a region of interest in the patient's body. Because the transducer array is two-dimensional, the receive scan lines can be steered in azimuth and in elevation to form a three-dimensional scan pattern. The beamformer 20 may, for example, be a digital beamformer such as may be found in any suitable commercially available medical diagnostic ultrasound machine.

The beamformer signals are stored in an image data buffer 22 which, as described below, stores image data for different volume segments of an image volume and for different points of a cardiac cycle, as discussed further herein. The image data is output from image data buffer 22 to a display system 24 which generates a three-dimensional image of the region of interest from the image data. The display system 24 may include a scan converter which converts sector scan signals from beamformer 20 to conventional raster scan display signals.

A system controller 26 provides overall control of the ultrasound diagnostic imaging system. The system controller 26 performs timing and control functions and typically includes a microprocessor and associated memory. In addition, an ECG device 28 includes ECG electrodes attached to a subject or patient. The ECG device 28 supplies ECG waveforms to system controller 26 for synchronizing imaging to the patient's cardiac cycle, as further described in detail below.

In operation, a contrast agent is injected into a patient's blood stream, for example, through the superior vena cava. The contrast agent improves a blood pool backscatter relative to tissue in the patient. In the display of an ultrasound image by display system 24, the blood appears black and the tissue appears white, wherein use of the contrast agent provides for an improved contrast between the blood and the tissue. As discussed herein, in one example, ultrasound energy is applied to the heart 30 via the ultrasound probe 16, and echoes are produced. The ultrasound echoes are received by the receiver 18 via the ultrasound probe 16 and resultant images are generated by the display system 24 of the ultrasound diagnostic imaging system 10. The images may then be used for diagnostic analysis. For example, the generated images may be used to make a determination of the various borders contained therein and to characterize the ejection fraction and volume calculations of the patient's heart.

Figure 2:
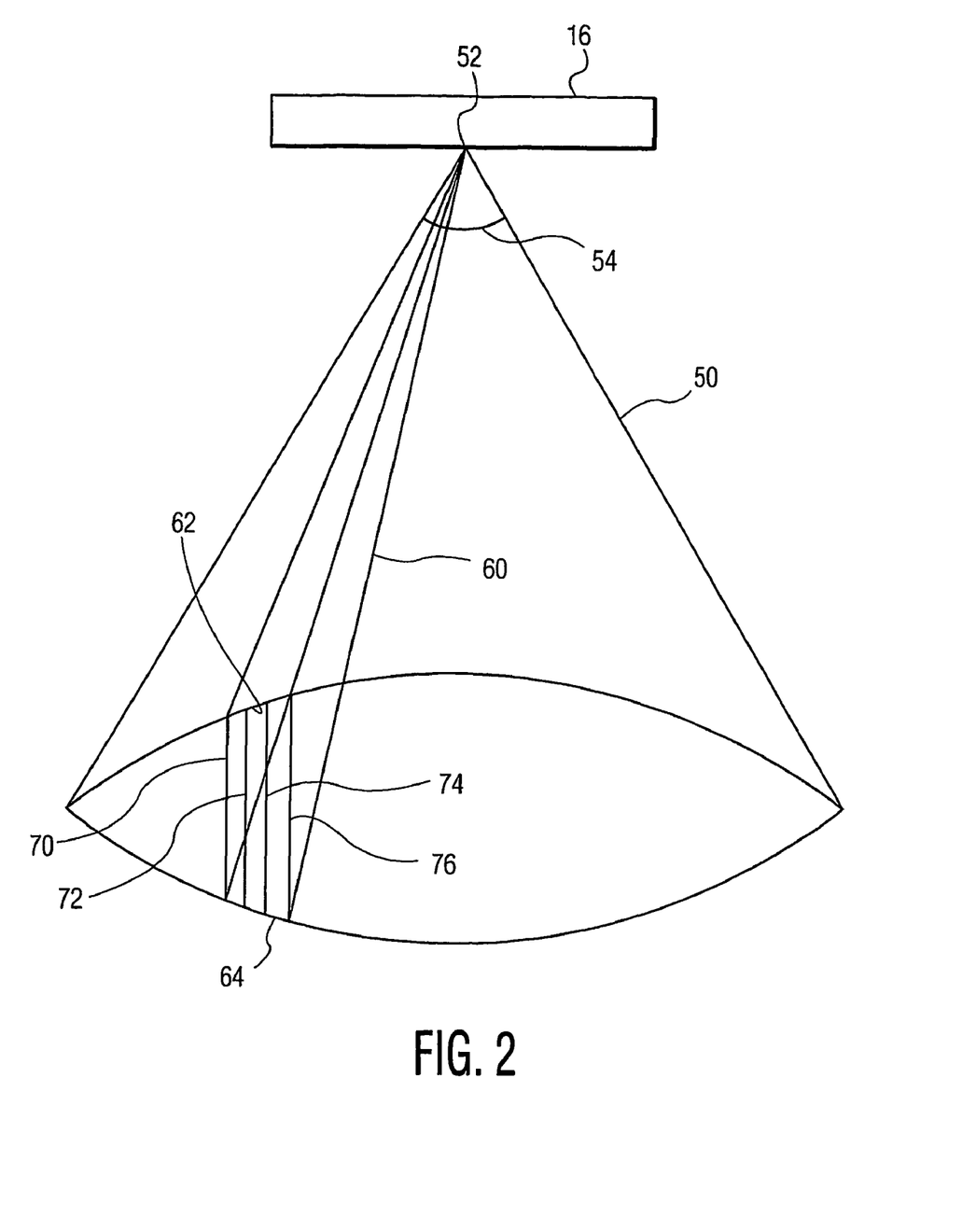
FIG. 2 is a schematic representation of a three-dimensional image volume and a volume segment of the image volume.

An example of a three-dimensional image volume 50 for which an image may be acquired in accordance with the present invention is shown in FIG. 2. Image volume 50 may have a conical shape with an apex 52 centered on transducer array 16. Image data for image volume 50 may be acquired by three-dimensional ultrasound imaging. Image volume 50 is further characterized by an angle indicated by reference numeral 54. Volume 50 may, for example, be imaged as a plurality of two-dimensional sector-shaped slices. The diameter of conical image volume 50 may be defined in terms of the required number of receive lines to achieve a desired resolution. The required number of receive lines to acquire a complete image of volume 50 is given by $\pi L^2/4$, where L is the diameter of conical image volume 50 in units of receive lines. Thus, for example, where image volume 50 has a diameter of 120 receive lines, 11,304 receive lines are needed to acquire image data for volume 50.

Figure 4:
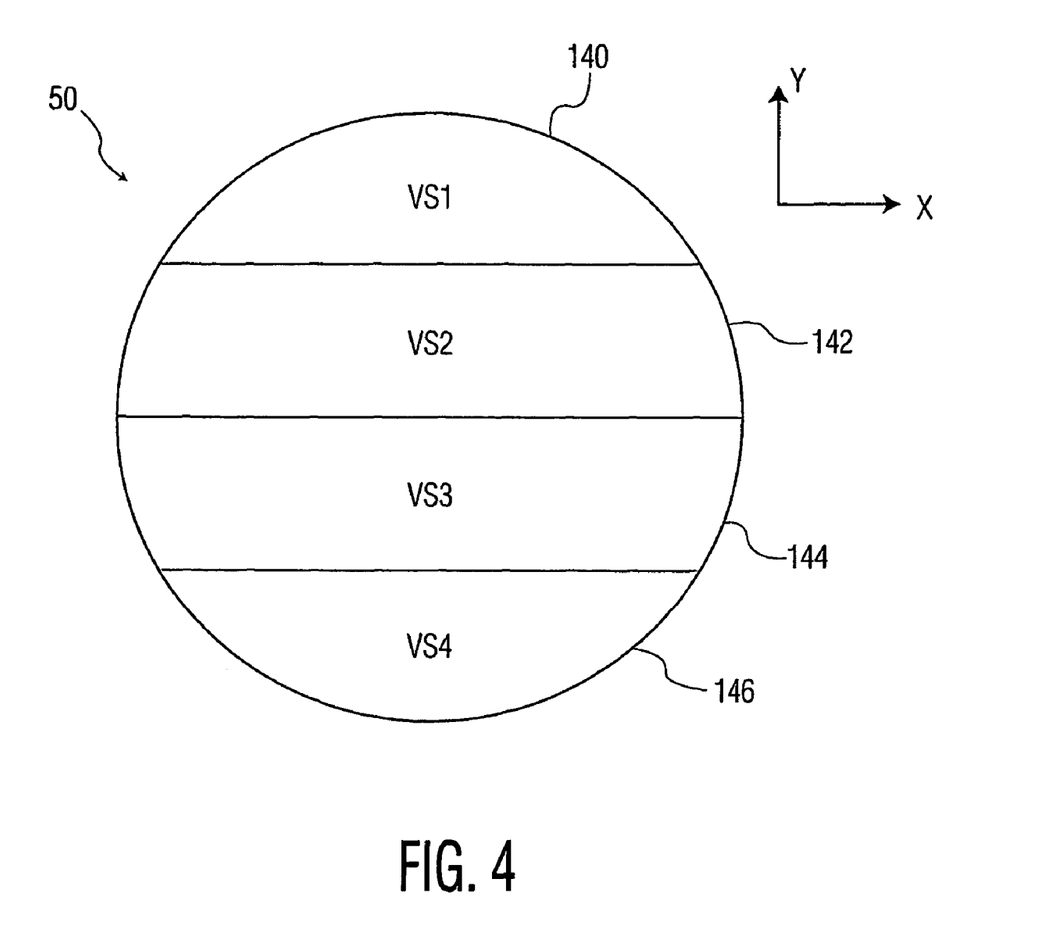
FIG. 4 is a cross-sectional view of a three-dimensional image volume that is divided into N volume segments, where N equals 4.

In one embodiment of the present disclosure, the ultrasound diagnostic imaging relates to cardiac imaging. To facilitate cardiac imaging, image volume 50 may be divided into three-dimensional volume segments for imaging of a patient's heart. FIG. 4 provides an example of a volume segment. Volume segment 60 is a three-dimensional slice of conical image volume 50 from a first side 62 to a second side 64, and may be imaged as a series of two-dimensional sector-shaped slices 70, 72, 74 and 76. The entire image volume 50 is divided into volume segments, as discussed further herein.

The volume segments which constitute image volume 50 may have any desired size and shape. Thus, for example, the cross-sections of the volume segments may be square, rectangular, circular, or irregularly shaped. Furthermore, different volume segments may have different sizes and shapes within a single image volume. In addition, the volume segments are not necessarily imaged as a series of two-dimensional slices. A sufficient number of transmit and receive lines are utilized to obtain a desired image resolution, using an imaging protocol suitable for a desired pattern. For a given image volume, the selection of the size, shape and number of volume segments may be based in part on the time available for image data acquisition during a specified cardiac phase as described below. Image data corresponding to different volume segments may be acquired with different apertures of transducer array 16.

It will be understood that the image volume itself is not limited to a conical shape and may have a variety of different shapes and sizes. For example, the image volume may be a pyramid or a truncated pyramid. The selection of the size and shape of the image volume may be based on the application and the type of transducer being utilized.

Figure 3:
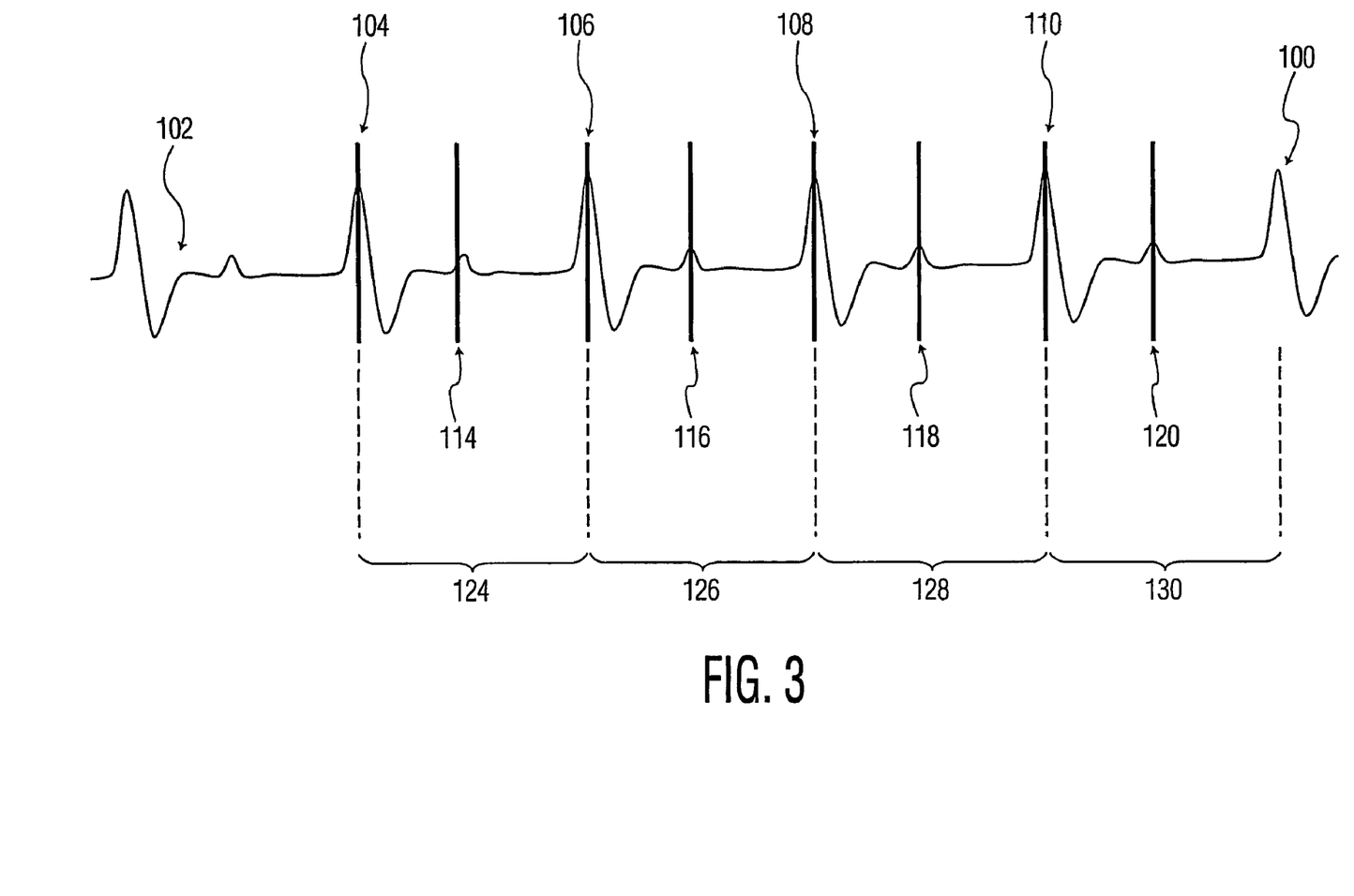
FIG. 3 is an illustrative view of an ECG waveform and a dual triggering sequence in accordance with one embodiment of the present disclosure.

According to one embodiment of the present disclosure, one feature of the invention is based on a dual triggered acquisition of image data for various volume segments in synchronism with the end diastole and end systole phases of a patient's cardiac cycle. An example of an ECG waveform is shown in FIG. 3. In the example of FIG. 3, ECG waveform 100 indicates a heartbeat at approximately every 830 milliseconds. According to one embodiment of the present disclosure, ultrasound image data acquisition trigger points are selected to occur subsequent to an acquire signal point (102) as follows. The trigger points occur at the end diastole (104, 106, 108, and 110) and the end systole (114, 116, 118, and 120) of corresponding cardiac cycles (124, 126, 128, and 130) of the ECG waveform 100. That is, in a dual trigger embodiment of the present disclosure, a first trigger of a cardiac phase corresponds to the end diastole and a second trigger corresponds to the end systole of the cardiac phase, for each cardiac phase of the acquisition until a full volume is acquired for both phases.

By obtaining a three-dimensional full volume image representing the heart cumulatively at each of the trigger points of the successive cardiac phases, quantitative information can be obtained. The three-dimensional images of the heart at respective successive trigger points of the cardiac phases can be displayed. The end systole and end diastole images can then be analyzed and diagnostics performed. Images for a selected portion of the cardiac phase can be rotated to a desired orientation for improved analysis. Image analysis techniques can be utilized to quantify maximum and minimum volumes of the left ventricle. From this information, ejection volume and ejection fraction can be calculated, using methods known in the art.

In accordance with an aspect of the invention, image data for three-dimensional volume segments of the image volume is acquired during successive cardiac cycles until a complete image is acquired. The ECG waveform of the patient is used to trigger image data acquisition, so that data acquisition is synchronized to the patient's cardiac cycle. More specifically, image data acquisition is synchronized to first and second trigger points within the cardiac cycle. In other words, image data is acquired during a cardiac cycle at a corresponding phase triggered by the end diastole and the end systole of the respective cardiac cycle. The amount of image data acquired during each cardiac phase is a function of the duration of the cardiac phase and the speed of image data acquisition.

According to one embodiment of the present disclosure, image data for a complete three-dimensional image of the image volume can be acquired in four heartbeats. Image data for each volume segment may be acquired responsive to first and second triggers during a corresponding single cardiac cycle. That is, image data acquisition for a specified volume segment is repeated during each cardiac phase. Thus, in four heartbeats a complete three-dimensional image may be acquired for each of the two trigger points of the four cardiac cycles. The image data from the four three-dimensional subvolumes for each of the two trigger points may be stored in image data buffer 22 (FIG. 1) and combined into images following data acquisition. The total acquisition time in this example is less than 3.5 seconds, thereby minimizing motion problems and allowing image data to be acquired in one breathold.

Different imaging protocols may be used to acquire volume segment image data. An example of an imaging protocol using abutting volume segments is shown in FIG. 4. A cross section of conical image volume 50 is shown. Volume segments 140, 142, 144, and 146 comprise abutting, three-dimensional slices of the conical image volume. Each of the volume segments 140, 142, 144, and 146 may be imaged as a series of two-dimensional sector-shaped slices. Four volume segments constitute the image volume 50 in this example. The volume segments may be imaged in any desired order. In one embodiment, abutting volume segments are imaged in succession, i.e., volume segment 140, followed by volume segment 142, followed by volume segment 144, etc. By imaging abutting segments in succession, adjacent image data are acquired from either the same cardiac cycle or consecutive cardiac cycles. Thus, discontinuities in the image data are minimized. In the imaging protocol of FIG. 4, a high resolution, three-dimensional image of the image volume is available after four heartbeats.

Figure 5:
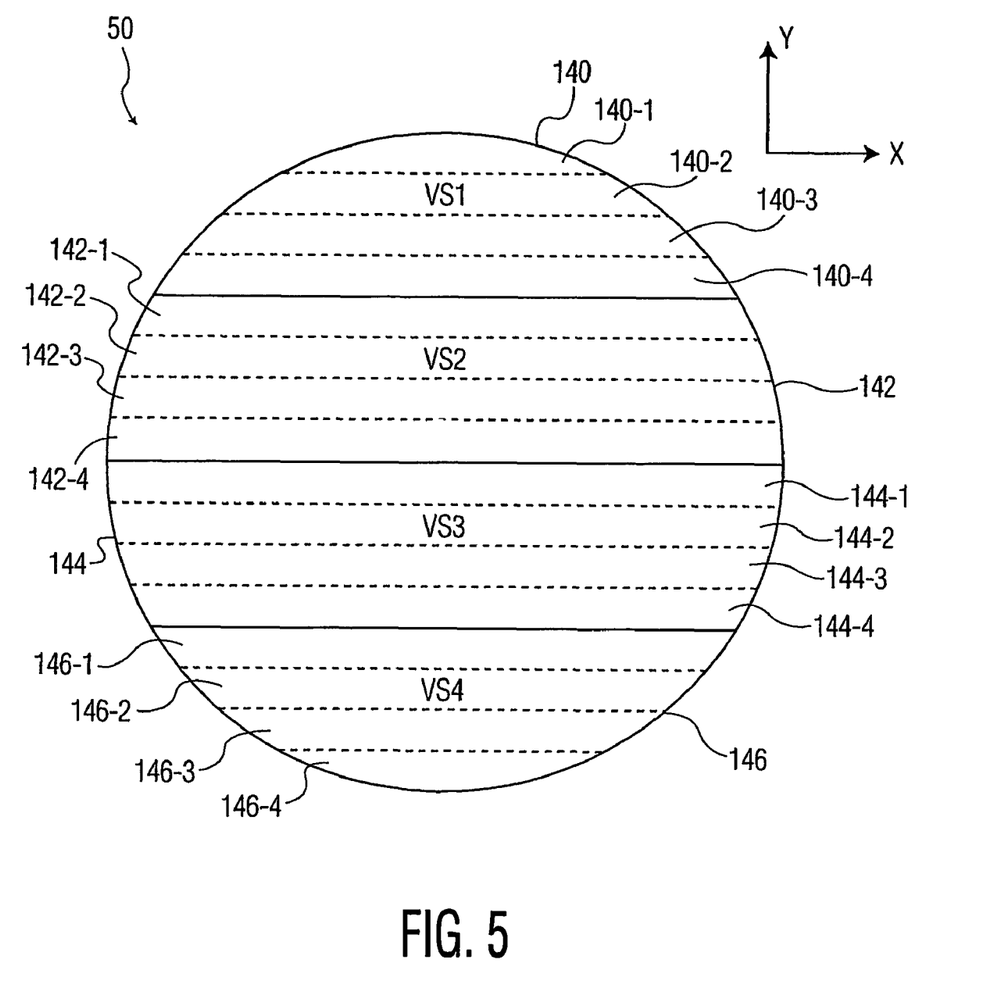
FIG. 5 is a cross-sectional view of the three-dimensional image volume of FIG. 4, wherein each volume segment further being divided into N subvolume segments.

The embodiments of the present disclosure also include other acquisition schemes to minimize the effects of microbubble destruction. One alternate scheme entails dividing each subvolume as displayed in FIG. 5 into multiple subvolumes. For example, the four subvolumes in FIG. 5 could be divided into 4 additional subvolumes each. An acquisition sequence could then consist of acquiring "interleaved" subvolumes during each cardiac cycle. For example, cardiac cycle number 1 could acquire subvolume 1 from VS1, subvolume 1 from VS2, subvolume 1 from VS3 and finally subvolume 1 from VS4. The second cardiac cycle could consist of a sequence of subvolume 2 from VS1, subvolume 2 from VS2, subvolume 2 from VS3 and finally subvolume 2 from VS4. The third cardiac cycle could consist of a sequence of subvolume 3 from VS1, subvolume 3 from VS2, subvolume 3 from VS3 and finally subvolume 3 from VS4. The fourth cardiac cycle could consist of a sequence of subvolume 4 from VS1, subvolume 4 from VS2, subvolume 4 from VS3 and finally subvolume 4 from VS4. These subvolumes can be combined to give a high resolution full volume image. The potential advantage with this technique is that smaller areas of microbubbles are depleted during subvolume data acquisition and therefore the areas of depleted microbubbles will be replenished with new microbubbles more quickly.

Another alternate acquisition scheme entails using different subvolumes for the different trigger points. Once again, using the example from FIG. 5, in the first cardiac cycle VS1 could be acquired at end-diastole (ED) and VS3 at end systole (ES) of the first cardiac cycle. The second cardiac cycle could consist of acquiring VS2 during ED and VS4 during ES of the second cardiac cycle. The third cardiac cycle could consist of acquiring VS3 at ED and VS1 at ES. The fourth could consist of acquiring VS4 during ED and VS2 during ES. One benefit of this technique over that of acquiring the same subvolume twice in the same cardiac cycle is that the time between shooting the same subvolume is increased and therefore there is more time for destroyed contrast agent to be replaced.

Yet another possible acquisition scheme would consist of acquiring only one subvolume per cardiac cycle. In this case, however, it would take twice as long to acquire the full volume.

With respect to ultrasound systems having live 3D imaging capabilities, it is possible to make acquisitions of volumes of data with a relatively high frame rate. Accordingly, 3D imaging provides for the possibility of obtaining more accurate LV volume calculations over that of 2D imaging. However, other issues still remain. In order to acquire a volume data set that includes the entire heart it is necessary to acquire sub-volumes from different cardiac cycles and to "piece together" the sub-volumes. Also, image quality in three dimensions (3D) is proving to be more difficult than in two dimensions (2D). Accordingly, it is often more difficult to visualize endocardial borders in 3D than they are for 2D.

Real-time imaging of contrast agents in two dimensions has been shown to destroy the contrast agents at relatively low acoustic outputs. MI is a standard measure of output acoustic power. The FDA limit is 1.9 and is represented by the equation: MI=Peak Negative Pressure (MPa)/Frequency (MHz). A mechanical index (M) on the order of as low as 0.1 is often necessary to fully eliminate this destruction at normal frame rates (15-20 Hz). However, to further minimize microbubble exposure to ultrasound and subsequent destruction it is necessary to slow down the frame rate (e.g., below 15-20 Hz).

A primary symptom of contrast agent destruction is a corresponding reduction of contrast signal from end-diastole to end-systole during a cardiac cycle. This reduction of contrast signal causes an overestimation of ejection fraction due to an underestimation of end-systolic volume. A second symptom of contrast agent destruction is inhomogeneous filling of the LV cavity, wherein this second symptom can also cause incorrect volume calculations.

At MI's that are as low as 0.1, multi-pulse contrast specific detection techniques have been designed to reduce or subtract "linear" tissue signal to allow for an increase in contrast-to-tissue ratio. These techniques have dramatically increased endocardial visualization throughout the cardiac cycle by reducing and even eliminating contrast agent destruction. However, these techniques also cause a dramatic decrease in frame rates and will thus be more difficult to apply to full volume 3D imaging.

According to an embodiment of the present disclosure, the ultrasound method and apparatus utilizes a sequence of triggered sub-volumes with contrast to allow for the accurate assessment of end-diastolic and end-systolic volumes. By using dual triggering of the sub-volumes, it is even possible to raise the MI above 0.1 or so to a level that allows better signal-to-noise without as much microbubble destruction as there would be with real-time imaging rates. By acquiring ultrasound imaging data over a few cardiac cycles, a full volume can be obtained with the additional benefit of allowing time for destroyed microbubbles to be replaced with new microbubbles. This allows for making it much easier to visualize endocardial borders and paves the way for accurate assessment of end-diastolic and end-systolic volumes and thus ejection fraction with ultrasound. In other words, in light of the microbubble destruction, there are certain triggering sequences that can make ultrasound diagnostic imaging measurements with contrast more robust. One example of such a triggering sequence is provided in the present disclosure.

Dual triggering includes firing two ultrasound frames per cardiac cycle at predefined delays from the R-wave. For example, one frame is selected to be fired at zero (0) msec delay (corresponding to end-diastole) and a second frame is selected to be fired at end-systole (corresponding to on the order of about 300 msec after R-wave, depending upon the particular patient's heart rate). Full volume acquisition includes acquiring a full volume of data over multiple cardiac cycles. It is necessary to use multiple cardiac cycles since it is not possible to acquire the entire volume at a fast enough rate (within 50 msec). This is basically due to the speed of sound which limits how quickly lines can be acquired. Full volume mode acquires a smaller volume (i.e., a subvolume) at a fast rate. For example, ¼ of the volume is acquired at 20 Hz rate for one cardiac cycle, the next ¼ of the volume is acquired during the next cardiac cycle, etc.

In accordance with one embodiment of the present disclosure, combining dual trigger with a triggered full volume acquisition limits an overall exposure of contrast agent microbubbles to ultrasound in a desired manner, and thus keeping the echo signal received from the microbubbles from diminishing appreciably. It has been determined that the acoustic levels of ultrasound as low as an MI of 0.1 are high enough to "destroy" the contrast agent microbubbles. Accordingly, instead of acquiring ¼ of the volume of interest at a fast rate, the volume is acquired at a slower rate, for example, ¼ at end diastole and ¼ at end systole. This means only 2 subvolumes may be acquired during one cardiac cycle as opposed to 12 or more subvolumes that are acquired without dual triggering. By altering the data acquisition with the dual triggering at end diastole and end systole, the cardiac contraction information is lost; however, the important information of the left ventricular (LV) volumes will be represented more accurately. It is also possible to acquire the subvolumes at a slower rate by having more than 2 triggers per cardiac cycle or by delaying between each subvolume. This decrease in volume rate will reduce bubble destruction but will increase time resolution over dual triggered mode. Advantageously, the present embodiments utilize dual triggering sequences as discussed herein, in addition to the use of 3D ultrasound imaging with contrast, to determine cardiac volumes/ejection fraction. Accordingly, an improved quantification of cardiac volumes/ejection fraction can be obtained.

According to the embodiments of the present disclosure, it is possible to decrease contrast destruction and increase the ability to visualize the endocardial borders by "artificially" reducing the acquisition rate. Typically, the acquisition rate is determined by the speed of sound and the system's ability to acquire data as quickly as possible. This is particularly true of what would be done in 3D, since with 3D it is now necessary to acquire an entire volume rather than a plane of data. In fact, in order to acquire a large volume with a fast enough update rate for cardiac imaging (i.e., 15 volumes per second or higher), it is not only necessary to acquire a smaller volume in order to maintain the fast update rate, but also to then acquire the entire volume over multiple cardiac cycles.

For example, if a 20 "volume per second" update rate is deemed adequate for the patient's heart rate (say 60 beats per minute), then the subvolume size should be small enough to allow for this update rate. In the case of 60 beats per minute, each cardiac cycle is one second long and there will be 20 instances of the same subvolume acquired during the cardiac cycle. The next cardiac cycle will acquire a different subvolume, but there will also be 20 instances of that subvolume. In the end, after all desired subvolumes are acquired, they are "pieced" together to form a "full volume" at a high update rate of 20 volumes per second. It is critical that these subvolumes are acquired synchronized to the ECG, since the subvolumes are from different cardiac cycles and could have "seams" or artifacts if the heart is not in the same phase each time.

To increase contrast intensity by minimizing effects of microbubble destruction, an acquisition rate that is lower than the maximum rate (i.e., that set by the speed of sounds as well as the setup time of the electronics) will help. Use of a dual trigger is an example of how the acoustic exposure of microbubbles can be limited since only two subvolumes are acquired per cardiac cycle, rather than 20 as described above. However, it may be possible to acquire 3 or more instances of a subvolumes per cardiac cycle and still obtain a significant increase in contrast intensity, wherein an overall microbubble destruction amount is maintained below a given threshold amount.

The embodiments of the present disclosure can also be extended to right ventricle (RV) volumes and multi-pulse contrast techniques by acquiring over more cardiac cycles.

Figure 6:
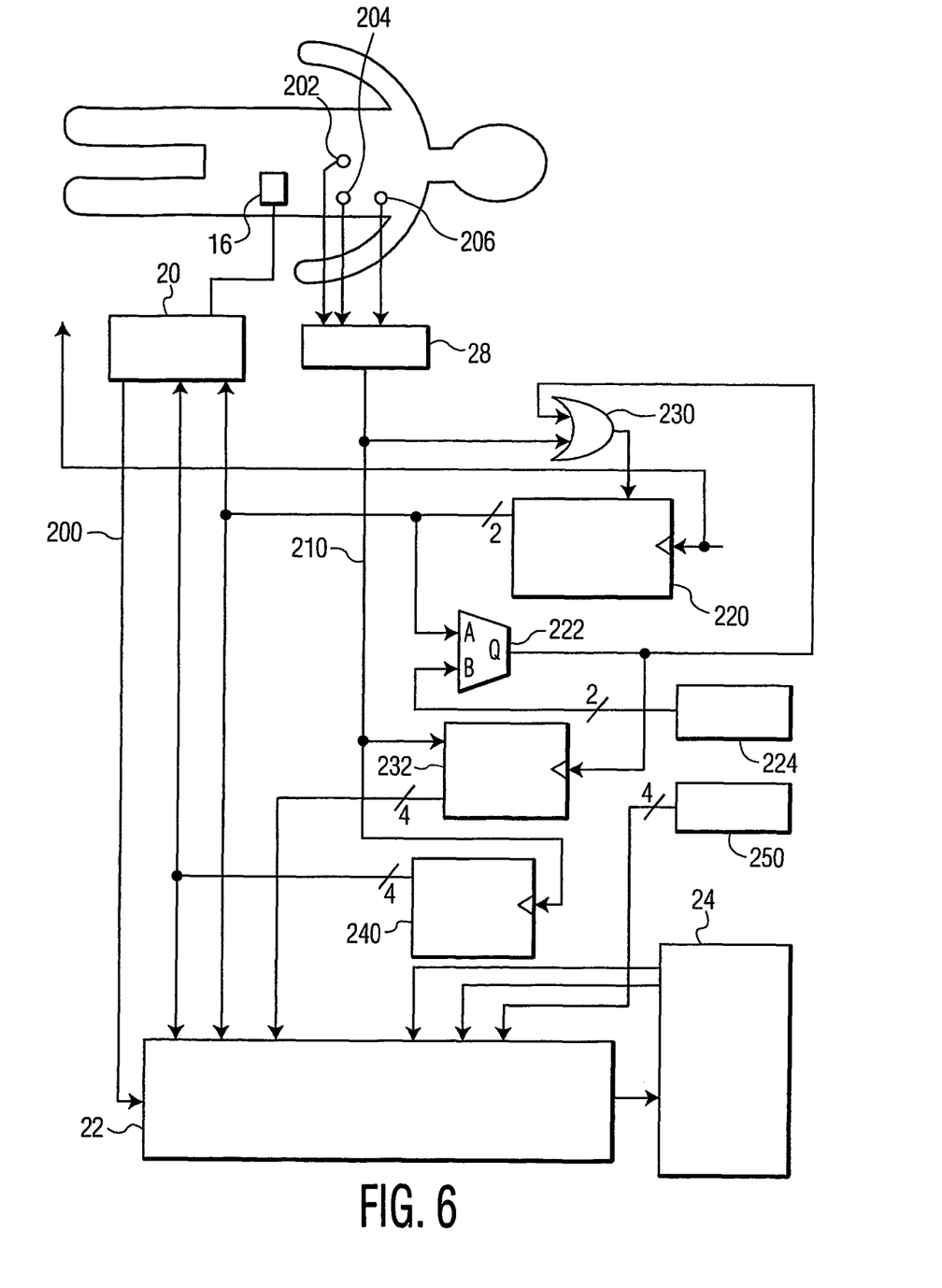
FIG. 6 is a schematic block diagram view of an ultrasound diagnostic imaging system according to one embodiment of the present closure.

A simplified block diagram of an example of a system for implementing segmented, three-dimensional cardiac imaging in accordance with the present embodiments is shown in FIG. 6. Like elements in FIGS. 1 and 6 have the same reference numerals. Ultrasound energy is transmitted into the region of interest in the patient by transducer array 16. Transmitter 12, T/R switch 14 and receiver 18 are omitted from FIG. 6 for ease of understanding. The received ultrasound echoes are processed by beamformer 20 to provide image data on line 200. The image data are stored in image data buffer 22, which in the example of FIG. 6 is a dual port random access memory (RAM).

ECG electrodes 202, 204 and 206, attached to the patient, sense the patient's cardiac cycle and provide signals to ECG device 28. The ECG device 28 provide an R-wave trigger output on line 210. The R-wave trigger output corresponds to the ECG waveform shown in FIG. 3.

A transmit trigger clock, which provides one pulse for each transmit event, is supplied to a transmit event counter 220 and to transmitter 12 (FIG. 1). The outputs of transmit event counter 220 are supplied to beamformer 20, to an event input address of image data buffer 22 and to a first input of a comparator 222. A register 224 stores the number of transmit events per cardiac phase. The outputs of register 224 are supplied to a second input of comparator 222. The output of comparator 222 is asserted when transmit event counter 220 reaches a count equal to the value stored in register 224. Thus, the output of comparator 222 is asserted when the required number of transmit events has been reached in each cardiac phase. The output of comparator is supplied to a first input of OR gate 230 and to the clock input of a cardiac phase counter 232. The outputs of phase counter 232, which indicate the cardiac phase for which image data is being acquired, are supplied to a phase input address of image data buffer 22.

The R-wave trigger output of ECG device 28 is supplied to a second input of OR gate 230, to the reset input of phase counter 232 and to the clock input of a heartbeat counter 240. The heartbeat counter 240 is incremented by the patient's heartbeats. The outputs of heartbeat counter 240 are supplied to a segment input address of image data buffer 42 and indicate the volume segment for which image data is being acquired. Thus, the input address of image data buffer 22 is made up of a segment input address which indicates volume segment, a phase input address which indicates cardiac phase and an event input address which indicates the transmit event within a specific volume segment and cardiac phase. The dual port RAM of image data buffer 22 may have locations for storage of image data corresponding to each transmit event of each volume segment of the image volume and corresponding to each phase of the patient's cardiac cycle.

The OR gate 230 supplies an output to the reset input of transmit event counter 220. Thus, transmit event counter is reset by the patient's heartbeat or when the comparator 222 indicates that the required number of transmit events has been completed for the current cardiac phase.

The output from image data buffer 22 is controlled by display system 24. Image data buffer 22 receives an output address, including a segment output address and an event output address from display system 24, and a cardiac phase output address from a register 250. Register 250 contains a value that indicates the cardiac phase to be displayed. The display system 24 combines the image data for the volume segments of the selected cardiac phase to produce a three-dimensional image of the image volume. By incrementing the value in register 250, three-dimensional images of different cardiac phases may be displayed in sequence. By incrementing to successive images at a suitable rate, images of heart movement may be displayed.

The control components of the imaging system of FIG. 6, including transmit event counter 220, comparator 222, OR gate 230, phase counter 232, heartbeat counter 240 and registers 224 and 250, may constitute part of system controller 26 (FIG. 1). It will be understood that the functions performed by these control components may be performed by a programmed microcomputer, microcontroller, or the like, for performing the embodiments of the present disclosure.

Figure 7:
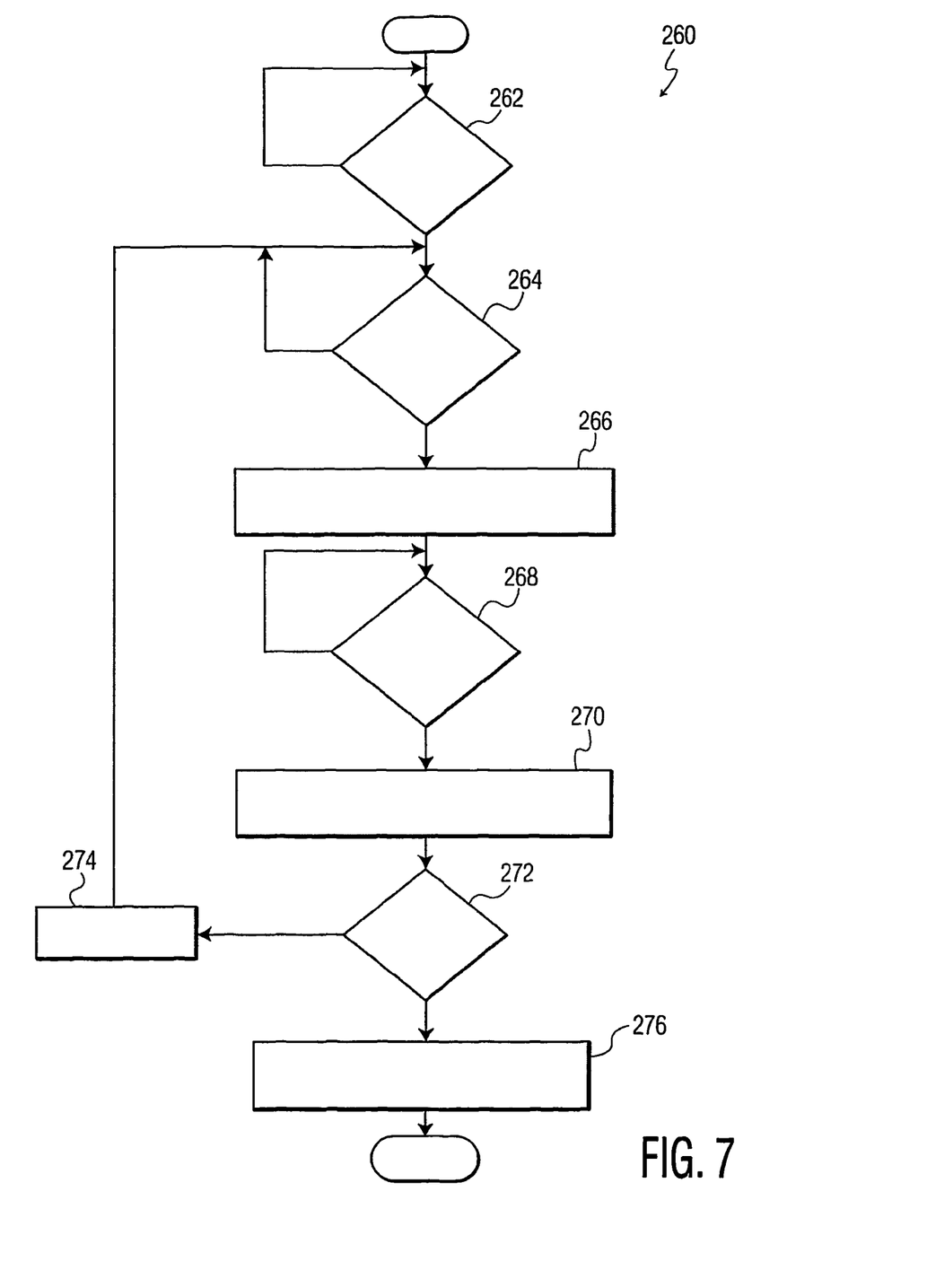
FIG. 7 is a flow diagram of an example of a method for cardiac ultrasound imaging according to one embodiment of the present disclosure.

A flowchart of a process for segmented three-dimensional cardiac imaging in accordance with one embodiment of the present disclosure is shown in FIG. 7. The process begins at step 262 a query whether an ECG trigger pulse is received. If no ECG trigger pulse is received, the query continues to loop to itself. On the other hand, if an ECG trigger pulse is received, indicative of an acquire trigger of the ECG waveform, the process proceeds to step 264. At step 264, the process queries whether the end diastole of the cardiac cycle has occurred. If not, then the query repeats itself. Upon occurrence of the end diastole of the cardiac cycle, the process advances to step 266. Occurrence of the end diastole of the cardiac cycle is marked by the triggering of an acquisition pulse. Responsive to the ECG trigger at end diastole, as per step 264, image data is acquired at step 266 for volume segment i at the end diastole phase of the cardiac cycle. The data acquisition step 266 involves generation of the specified number of transmit events for the volume segment, processing the received signals in beamformer 20 to provide image data and storing the image data in image data buffer 22.

At step 268, the process queries whether the end systole of the cardiac cycle has occurred. If not, then the query repeats itself. Upon occurrence of the end systole of the cardiac cycle, the process advances to step 270. Occurrence of the end systole of the cardiac cycle is marked by the triggering of an acquisition pulse. Responsive to the ECG trigger at end systole, as per step 268, image data is acquired at step 270 for volume segment i at the end systole phase of the cardiac cycle. The data acquisition step 270 involves generation of the specified number of transmit events for the corresponding volume segment, processing the received signals in beamformer 20 to provide image data and storing the image data in image data buffer 22.

In step 272, a determination is made as to whether the current subvolume segment is the last of the subvolume segments for the particular ultrasound diagnostic image acquisition. In the example of the ECG waveform of FIG. 3, there are four (4) subvolumes. Accordingly, the last subvolume segment would not be reached until after four subvolumes have been acquired. Accordingly, responsive to the last subvolume segment not yet being reached, the process proceeds to step 274 with the incrementing of subvolume i and then returning to step 264 to await receipt of a next end diastole trigger of a next cardiac cycle and proceeding therefrom On the other hand, responsive to the last subvolume segment being reached at step 272, the process proceeds to step 276 with the combining of subvolume image data for the cardiac cycles and thereafter ending.

The process of FIG. 7 performs image data acquisition for the end diastole and end systole triggered volume segments during each of the patient's cardiac cycles of a given acquisition period. Complete three-dimensional images of each end diastole and end systole triggered portions of subvolumes for a complete volume are acquired in a relatively small number of heartbeats. When image data for all subvolume segments of the image volume has been acquired, the volume segment image data is combined in step 276 to provide a composite image for each of the end diastole and end systole triggered portions of the cardiac cycles. The combining step involves combining image data for the subvolume segments of the image volume from respective end diastole and end systole portions of the cardiac cycles.

Figure 8:
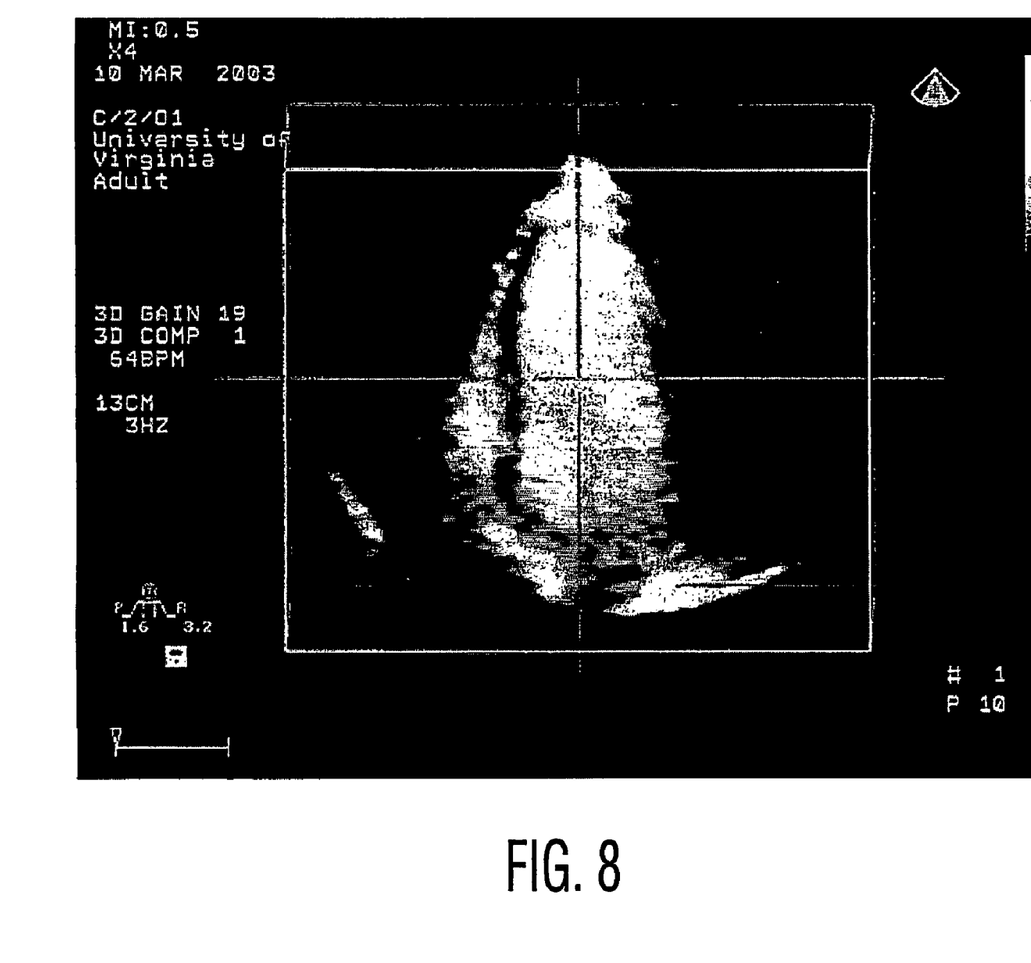
FIG. 8 is a display image view of a portion of a volume produced using the method and apparatus in accordance with one embodiment of the present disclosure.
Figure 9:
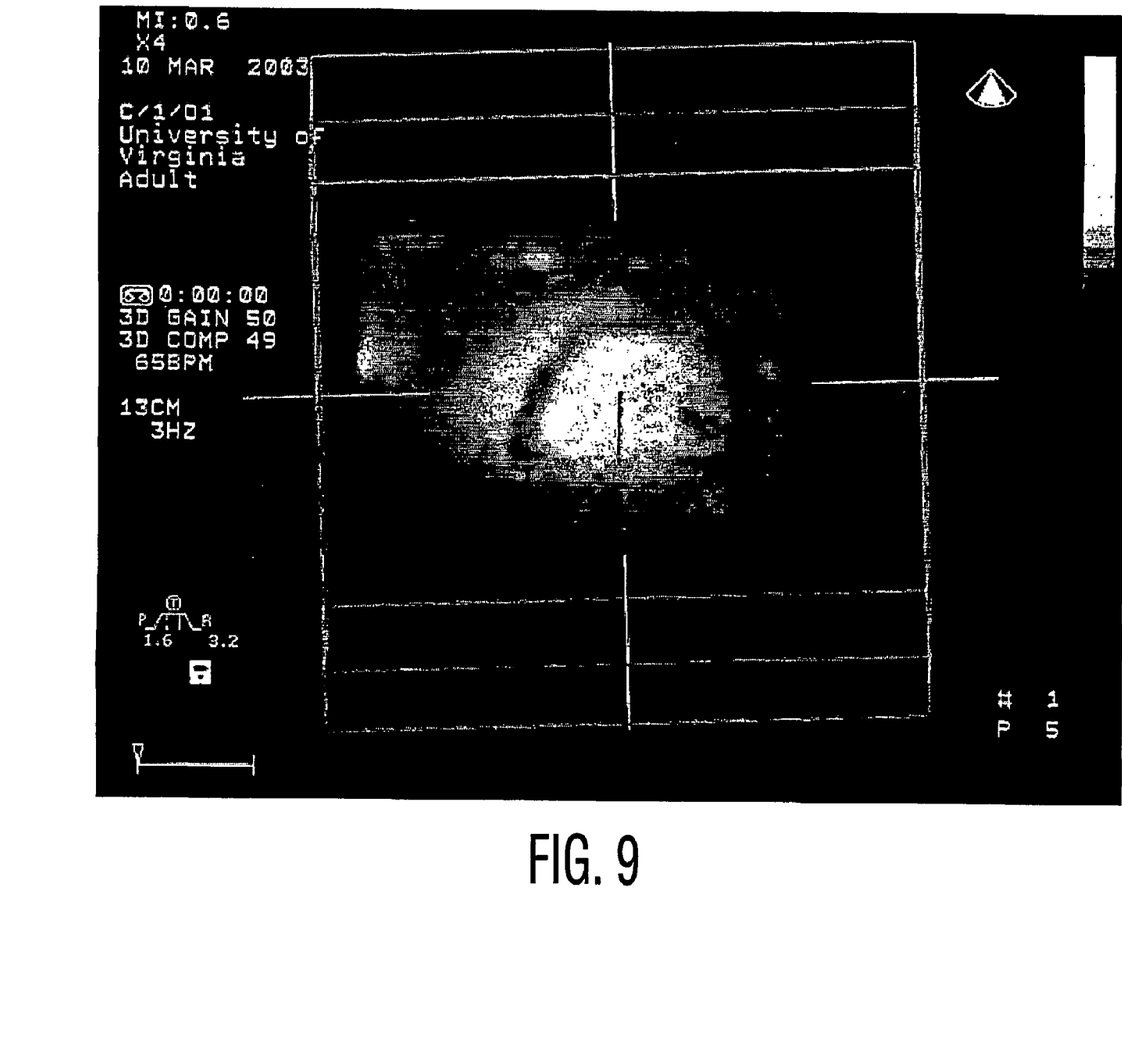
FIG. 9 is a display image view of another portion of a volume produced using the method and apparatus in accordance with one embodiment of the present disclosure.

FIGS. 8 and 9 illustrate display image views of first and second portions of a volume produced using the method and apparatus in accordance with one embodiment of the present disclosure. Cardiac boundaries are more readily discerned, the boundaries having been imaged by the dual triggered end diastole, end systole of a 3D full volume ultrasound image data acquisition with contrast according to the embodiments of the present disclosure. Accordingly, more accurate cardiac volume calculations and ejection fraction can be obtained.

The embodiments of the present disclosure have been described in connection with acquisition of image data using a digital beamformer. It will be understood that the embodiments may be applied to analog implementations of ultrasound imaging systems.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The invention claimed is:

1. A method of generating three-dimensional (3D) full volume ultrasound images with the use of contrast agents comprising:
acquiring ultrasound image data for multiple subvolumes synchronized to an ECG over multiple cardiac cycles via triggering, wherein the acquiring comprises using an output acoustic power insufficient for causing destruction of the contrast agents during ultrasound image data acquisition and using an output acoustic power sufficient for causing destruction of the contrast agents during ultrasound image data acquisition, wherein the triggering of respective ones of the ultrasound image data acquisitions of the multiple subvolumes is selected to enable destroyed contrast agents to be replaced by new contrast agents prior to a subsequent triggering of ultrasound image data acquisition of a subsequent subvolume; and
combining ultrasound image data from the multiple subvolumes to generate the 3D full volume ultrasound image data.

2. The method of claim 1, wherein triggering includes multiple triggering.

3. The method of claim 2, further wherein multiple triggering includes use of multiple triggers per cardiac cycle.

4. The method of claim 1, wherein triggering includes dual triggering with use of a first and a second trigger per cardiac cycle.

5. The method of claim 4, wherein the first trigger corresponds to the end-diastole (ED) of a cardiac cycle and the second trigger corresponds to the end-systole (ES) of the cardiac cycle.

6. The method of claim 1, further wherein the ultrasound image data for a portion of a first subvolume is acquired at end-diastole of a cardiac cycle and wherein the ultrasound image data for another portion of the first subvolume is acquired at end-systole of a cardiac cycle.

7. The method of claim 6, wherein ultrasound image data for the portion of the first subvolume is acquired in a first cardiac cycle and wherein ultrasound image data for the another portion of the first subvolume is acquired in another cardiac cycle.

8. The method of claim 1, wherein ultrasound image data for a portion of a first subvolume is acquired at end-diastole of a first cardiac cycle, and wherein ultrasound image data for a portion of a second subvolume is acquired at end-systole of the first cardiac cycle, and wherein ultrasound image data for another portion of the first subvolume is acquired at end-systole of another cardiac cycle, and wherein ultrasound image data for another portion of the second subvolume is acquired at end-diastole of another cardiac cycle.

9. The method of claim 1, further wherein acquisition of ultrasound image data of the subvolumes includes acquisition of ultrasound image data of interlaced subvolumes.

10. The method of claim 1, wherein ultrasound image data for N subvolumes is acquired over M cardiac cycles, wherein M and N are integers and M>N.

11. The method of claim 1 further wherein acquisition of ultrasound image data includes at least one selected from the group consisting of power Doppler, pulse inversion, power modulation, and combinations of the same.

12. The method of claim 1, wherein the 3D full volume images are that of a left ventricle (LV), wherein the method further comprising:
analyzing the ultrasound image data and producing a quantification of the left ventricle in response to the analyzed ultrasound image data.

13. The method of claim 12, wherein the quantification includes a cardiac volume and an ejection fraction.

14. A method of generating three-dimensional (3D) full volume ultrasound images with a contrast agent comprising:
acquiring ultrasound image data over multiple cardiac cycles, wherein acquiring the ultrasound image data includes acquiring, for each of the multiple cardiac cycles, ultrasound image data for a subvolume using dual triggering of a corresponding one of the multiple cardiac cycles for a respective subvolume, wherein the dual triggering enables a) a minimized destruction of microbubbles for an output acoustic power insufficient for causing destruction of microbubbles of the contrast agent during ultrasound image data acquisition, and b) replacement of destroyed microbubbles with new microbubbles of contrast agent for an output acoustic power sufficient for causing destruction of microbubbles of the contrast agent during ultrasound image data acquisition, prior to a subsequent triggering; and
combining ultrasound image data from the subvolumes to generate the 3D full volume ultrasound image data.

15. The method of claim 14, further comprising:
displaying a 3D full volume view in response to the 3D full volume ultrasound image data.

16. The method of claim 14, further comprising:
determining, in response to the 3D full volume ultrasound image data, at least one of a cardiac volume and an ejection fraction.

17. The method of claim 14, wherein the dual triggering is selected for minimizing an overall microbubble destruction effect of the contrast agent for acquisition of the subvolume ultrasound image data.

18. The method of claim 17, wherein the overall microbubble destruction effect includes a replacement of destroyed microbubbles with new microbubbles between an occurrence of a first trigger and a second trigger of dual triggered phases of the cardiac cycle.

19. The method of claim 18, wherein the first trigger corresponds to an end diastole of the cardiac cycle and wherein the second trigger corresponds to an end systole of the cardiac cycle.

20. The method of claim 14, wherein the multiple cardiac cycles include four successive cardiac cycles of the patient.

21. The method of claim 14, wherein the dual triggering includes acquiring subvolumes triggered at end diastole and end systole of each respective one of the multiple cardiac cycles.

22. The method of claim 21, wherein the dual triggering is selected for minimizing an overall microbubble destruction effect of the contrast agent for acquisition of the subvolume ultrasound image data, wherein the overall microbubble destruction effect includes a replacement of destroyed microbubbles with new microbubbles between an occurrence of a first trigger and a second trigger of dual triggered phases of the cardiac cycle, wherein the overall microbubble destruction effect includes a replacement of destroyed microbubbles with new microbubbles between an occurrence of a first trigger and a second trigger of dual triggered phases of the cardiac cycle, wherein the first trigger corresponds to an end diastole of the cardiac cycle and wherein the second trigger corresponds to an end systole of the cardiac cycle.

23. The method of claim 22, wherein the multiple cardiac cycles include four successive cardiac cycles of the patient.

24. A method for diagnostic ultrasound imaging comprising:
    introducing an ultrasound contrast agent into a patient, the ultrasound contrast agent providing microbubbles for enhancing a contrast level within acquired ultrasound image data;
    acquiring ultrasound image data representative of three-dimensional subvolume segments of an image volume of interest in the patient in synchronism with dual triggered phases of multiple cardiac cycles of the patient, wherein the dual triggering enables at a) a minimized destruction of microbubbles for an output acoustic power insufficient for causing destruction of microbubbles of the contrast agent during ultrasound image data acquisition, and b) replacement of destroyed microbubbles with new microbubbles of contrast agent for an output acoustic power sufficient for causing destruction of microbubbles of the contrast agent during ultrasound image data acquisition, prior to a subsequent triggering; and
    combining the image data of the subvolume segments to produce 3D full volume image data, wherein the dual triggered phases are selected to minimize an overall microbubble destruction effect of the contrast agent for the acquisition of the 3D subvolume segments.

25. The method of claim 24, further comprising:
    displaying a 3D full volume view in response to the 3D full volume ultrasound image data.

26. The method of claim 24, further comprising:
    determining, in response to the 3D full volume ultrasound image data, at least one of a cardiac volume and an ejection fraction.

27. The method of claim 24, wherein the overall microbubble destruction effect includes a replacement of destroyed microbubbles with new microbubbles between an occurrence of a first trigger and a second trigger of the dual triggered phases of the cardiac cycle.

28. The method of claim 27, wherein the first trigger corresponds to an end diastole of a cardiac cycle and wherein the second trigger corresponds to an end systole of the same cardiac cycle.

29. The method of claim 24, wherein the multiple cardiac cycles include four successive cardiac cycles of the patient.

30. The method of claim 24, wherein acquiring image data comprises synchronizing acquisition of the image data to two selected phases of the patient's cardiac cycle.

31. The method of claim 30, wherein the selected phases include end diastole and end systole phases of the cardiac cycle.

32. The method of claim 24, wherein acquiring image data comprises acquiring image data for the subvolume segments in synchronism with a number N of successive cardiac cycles of the patient.

33. The method of claim 32, wherein N is equal to 4.

34. Apparatus for ultrasound diagnostic imaging with a contrast agent comprising:
    a transducer including an array of transducer elements;
    a transmitter for transmitting ultrasound energy with said transducer into an image volume of interest in a patient's body as a plurality of transmit beams;
    a receiver for receiving ultrasound echos with said transducer from the image volume in response to the ultrasound energy and for generating received signals representative of the received ultrasound echos;
    a receive beamformer for processing the received signals to form at least one receive beam for each of the transmit beams and to generate image data representative of the ultrasound echos in the receive beam;
    an ECG device adapted for being coupled to the patient, and in response to being coupled to the patient, for generating an ECG signal representative of the patient's cardiac cycle;
    a controller responsive to the ECG signal for controlling said transmitter and said receive beamformer to acquire image data representative of three-dimensional volume segments of the image volume in synchronism with corresponding first and second triggered portions of cardiac cycles of the patient, each of the volume segments containing image data distributed in three dimensions, wherein image data representative of a volume segment is acquired during a single cardiac cycle of the patient, and wherein the first and second triggered portions provide triggering that enables a) a minimized destruction of microbubbles of a contrast agent for an output acoustic power insufficient for causing destruction of microbubbles of the contrast agent during ultrasound image data acquisition, and b) replacement of destroyed microbubbles of the contrast agent with new microbubbles of contrast agent for an output acoustic power sufficient for causing destruction of microbubbles of the contrast agent during ultrasound image data acquisition, prior to a subsequent triggering; and
    a combining circuit for combining the image data representative of the volume segments to provide image data representative of a three-dimensional ultrasound image of the image volume.

35. The apparatus of claim 34, wherein said transducer includes an electronically scanned two-dimensional array of transducer elements.

36. The apparatus of claim 34, wherein said controller further includes means for synchronizing acquisition of the image data to a selected phase of the patient's cardiac cycle.

37. The apparatus of claim 34, wherein said controller further includes means for acquiring image data for the volume segments in synchronism with the end diastole and end systole phases of N successive cardiac cycles of the patient, wherein N equals four.

38. A method for ultrasound diagnostic imaging with a contrast agent comprising:
    acquiring ultrasound image data representative of first and second three-dimensional volume segments of an image volume of interest in synchronism with selected first and second phases of the patient's cardiac cycle, each of the first and second volume segments containing image data distributed in three dimensions, wherein image data representative of each of the respective first and second volume segments is acquired during a single cardiac cycle of the patient, wherein acquiring includes use of dual triggering to enable a) a minimized destruction of microbubbles for an output acoustic power insufficient for causing destruction of microbubbles of the contrast agent during ultrasound image data acquisition, and b) replacement of destroyed microbubbles with new microbubbles of contrast agent for an output acoustic power sufficient for causing destruction of microbubbles of the contrast agent during ultrasound image data acquisition, prior to a subsequent triggering;

repeating the acquiring of ultrasound image data for N successive cardiac cycles of the patient, where N equals 4; and combining image data of respective first and second volume segments for respective cardiac phases to provide three-dimensional ultrasound images that are respectively representative of the end diastole and end systole phases of the N cardiac cycles.

* * * * *